US009387128B1

(12) United States Patent
Corder

(10) Patent No.: US 9,387,128 B1
(45) Date of Patent: Jul. 12, 2016

(54) BREASTFEEDING ASSISTANCE DEVICE

(71) Applicant: Allison M. Corder, Wadsworth, IL (US)

(72) Inventor: Allison M. Corder, Wadsworth, IL (US)

(*) Notice: Subject to any disclaimer, the term of this patent is extended or adjusted under 35 U.S.C. 154(b) by 0 days.

(21) Appl. No.: 14/257,417

(22) Filed: Apr. 21, 2014

(51) Int. Cl.
*A41D 1/20* (2006.01)
*A61F 13/14* (2006.01)

(52) U.S. Cl.
CPC ...................... *A61F 13/14* (2013.01)

(58) Field of Classification Search
CPC ... Y10T 428/24008; A41D 1/205; A41C 3/04
See application file for complete search history.

(56) References Cited

U.S. PATENT DOCUMENTS

| 4,844,103 | A | 7/1989 | Vick et al. | |
|---|---|---|---|---|
| 5,372,152 | A | 12/1994 | Dutch | |
| 5,776,177 | A | 7/1998 | MacWhinnie et al. | |
| 6,189,169 | B1 * | 2/2001 | Marcotte | 5/655 |
| 6,261,313 | B1 | 7/2001 | MacWhinnie et al. | |
| 2006/0156471 | A1 * | 7/2006 | Cazzini et al. | 5/482 |
| 2014/0259404 | A1 * | 9/2014 | Walker et al. | 5/485 |

* cited by examiner

*Primary Examiner* — Alexander Thomas
(74) *Attorney, Agent, or Firm* — Allison M. Corder, Esq.

(57) ABSTRACT

A breastfeeding assistance device configured to be shaped into a variety of configurations, or forms. The device being self-sustainable in any selected configuration including a configuration that compresses a breast to assist with breastfeeding while allowing at least one hand free.

19 Claims, 5 Drawing Sheets

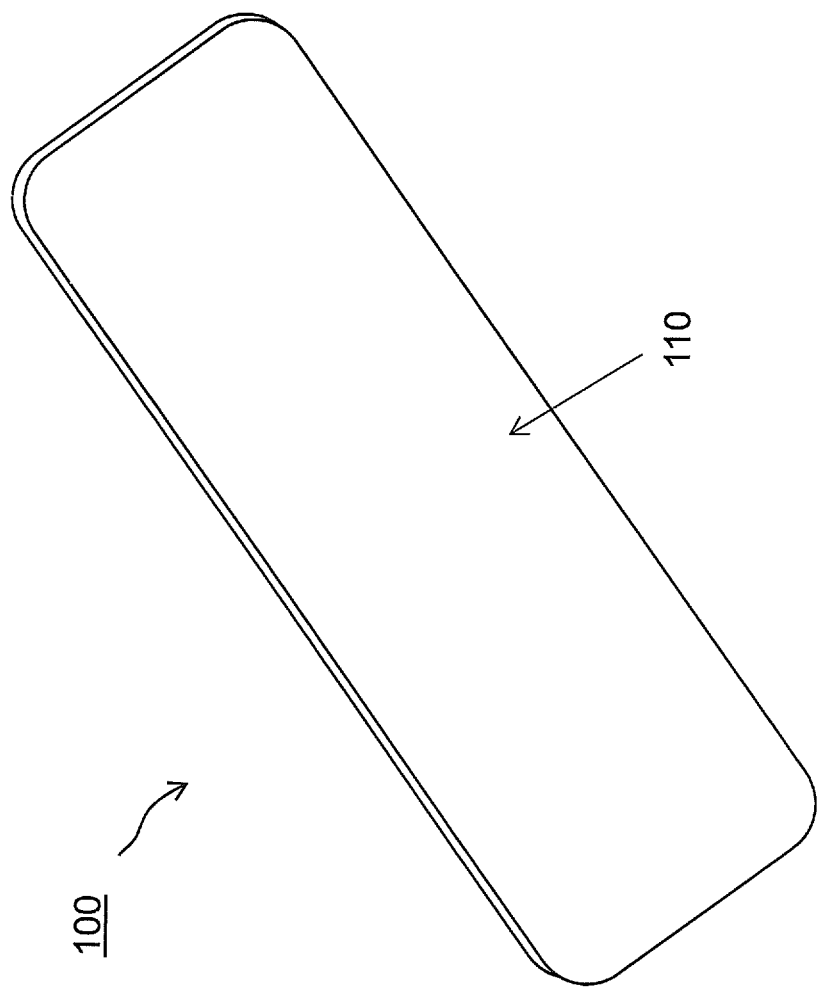

BREASTFEEDING ASSISTANCE DEVICE

FIELD OF THE INVENTION

The invention relates generally to breastfeeding along with items used during breastfeeding. More particularly, the invention is directed to a device that assists with breastfeeding while allowing at least one hand free.

BACKGROUND OF THE INVENTION

There are many advantages to breastfeeding for both the baby and the mother. In addition to breast milk providing vitamins and nutrients a baby needs, breast milk includes substances that may protect a baby from illness. Breast milk may also protect a baby from developing allergies and boost intelligence. Advantages of breastfeeding for the mother may include reducing stress, reducing risk of postpartum depression, and reducing risk of some types of cancer.

While breastfeeding, both hands of the mother are typically occupied—one hand to hold the baby and the other hand to manipulate the breast to either encourage proper latch-on, promote milk production, or prevent the breast from covering the nose of the baby or weighing on the baby's lower jaw and chin.

Proper latch-on of the baby on the breast promotes successful breastfeeding. Proper latch-on also prevents and resolves sore nipples. With proper latch-on, most of the mother's areola is positioned within the baby's mouth such that the mother's nipple goes to the back of the baby's mouth. The baby's gums compress the milk sinuses that sit about an inch behind the nipple. The baby's tongue is forward, underneath the breast, over the lower gum, and helps the baby draw out milk.

To facilitate proper latch-on, a mother may squeeze her breast in order for the baby to get as much of the areola in his or her mouth as possible.

A breastfeeding mother may also squeeze her breast to promote milk production. Breast compression, in some instances, is necessary in order to simulate a letdown reflex or to stimulate a natural letdown reflex to occur. In addition, breast compression may be necessary in order for the baby to get more milk including milk that is high in fat. When squeezing the breast to continue the flow of milk to the baby, the breast is typically held far back from the nipple with a thumb on one side of the breast and the other fingers on the other side of the breast.

A mother may also support her breast in a position that keeps the weight of the breast off the baby's lower jaw and chin or prevents the breast from covering the nose of the baby. For example, a mother with large breasts—by nature or as a result of milk production—may support her breast by placing a hand under her breast during breastfeeding so that the breast does not interfere with the baby's air supply or the baby's ability to get breast milk.

Depending on the baby's position, a mother may manipulate her breast using a "C" hold as shown in FIG. 1A or a "U" hold as shown in FIG. 1B to either encourage proper latch-on, promote milk production, or prevent the breast from covering the nose of the baby or weighing on the baby's lower jaw and chin.

Typically while breastfeeding, both hands of the mother are occupied—one hand holds the baby and the other hand manipulates the breast to assist with breastfeeding. With both hands occupied, no hand is free to perform one or more tasks, for example, interacting with a cell phone, a tablet, a remote control, a magazine, or even eating or drinking. Therefore, there is a need for a device that assists with breastfeeding while allowing at least one hand free. The invention satisfies this need.

SUMMARY OF THE INVENTION

The invention is a device that assists with the support and manipulation of a mother's breast during breastfeeding as well as allows at least one hand free. The device may be used for a variety of one or more reasons including, for example, to facilitate proper latch-on, promote milk production, or prevent the breast from covering the nose of the baby or weighing on the baby's lower jaw and chin.

The breastfeeding assistance device is pliant, or flexible, such that it is easily arranged into one of many forms, also referred to as configurations. The breastfeeding assistance device is arranged into a selected form by simply bending and/or twisting the device. Once manually shaped into the selected form, the breastfeeding assistance device is self-sustaining in that form. In other words, the device maintains a particular form until arranged into a new form.

The breastfeeding assistance device is generally thin making it discreet and compact. The device is also small and lightweight such that it can quickly and easily be transported.

The breastfeeding assistance device is of a shape and a size such that it is adjustable to different breast sizes. For example, the breastfeeding assistance device may have a length greater than its width, such as a rectangular shape, so that the device can be used with breasts of all sizes, one size fits all.

The breastfeeding assistance device comprises a flexible body. The flexible body comprises an exterior portion surrounding a core portion. The core portion is constructed of a material that can bend and twist in a variety of directions while having a tensile strength that allows for repeat bending and twisting without breaking.

The exterior portion surrounds the core portion and is constructed of a flexible material that it is connected to and covers a majority of the core portion. The exterior portion is substantially immovable relative to the core portions such that it moves in conjunction with the core portion. Ideally, the exterior portion is constructed from a material that is comfortable against skin while being non-absorbent or impermeable to fluids including, for example, breast milk.

In certain embodiments, the core portion and/or exterior portion may include temperature retentive properties or temperature conductive properties in order to permit the breastfeeding assistance device to emit warm or cold properties slow and steadily.

The present invention and its attributes and advantages will be further understood and appreciated with reference to the detailed description below of presently contemplated embodiments, taken in conjunction with the accompanying drawings.

DESCRIPTION OF THE DRAWINGS

The preferred embodiments of the invention will be described in conjunction with the appended drawings provided to illustrate and not to the limit the invention, where like designations denote like elements, and in which:

FIG. 2 illustrates a perspective view of a breastfeeding assistance device according to one embodiment of the invention.

DETAILED DESCRIPTION OF THE INVENTION

A breastfeeding assistance device is configured to be manually shaped into a variety of forms, or configurations. The device is self-sustainable in any selected configuration including a configuration that compresses a breast to assist with the support and manipulation of a mother's breast during breastfeeding while allowing at least one hand free.

As shown in FIG. 2, a breastfeeding assistance device 100 includes an elongate, generally thin rectangular body 110. Although the device 100 is shown as a rectangular body 110, any shape body that is longer than it is wide is contemplated, for example, oval or crescent.

Figure 1B:
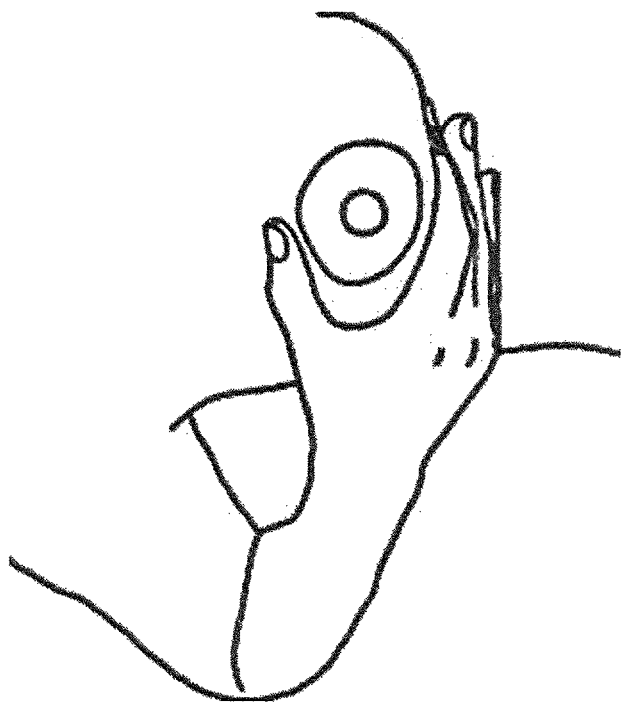
FIG. 1B illustrates a "U" hold used during breastfeeding.
Figure 1A:
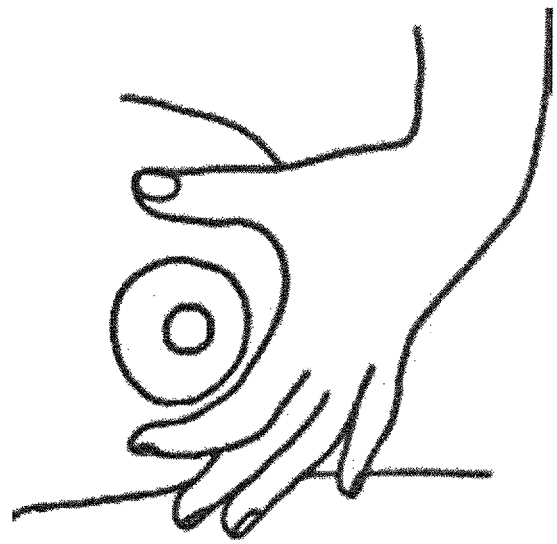
FIG. 1A illustrates a "C" hold used during breastfeeding.
Figure 3:
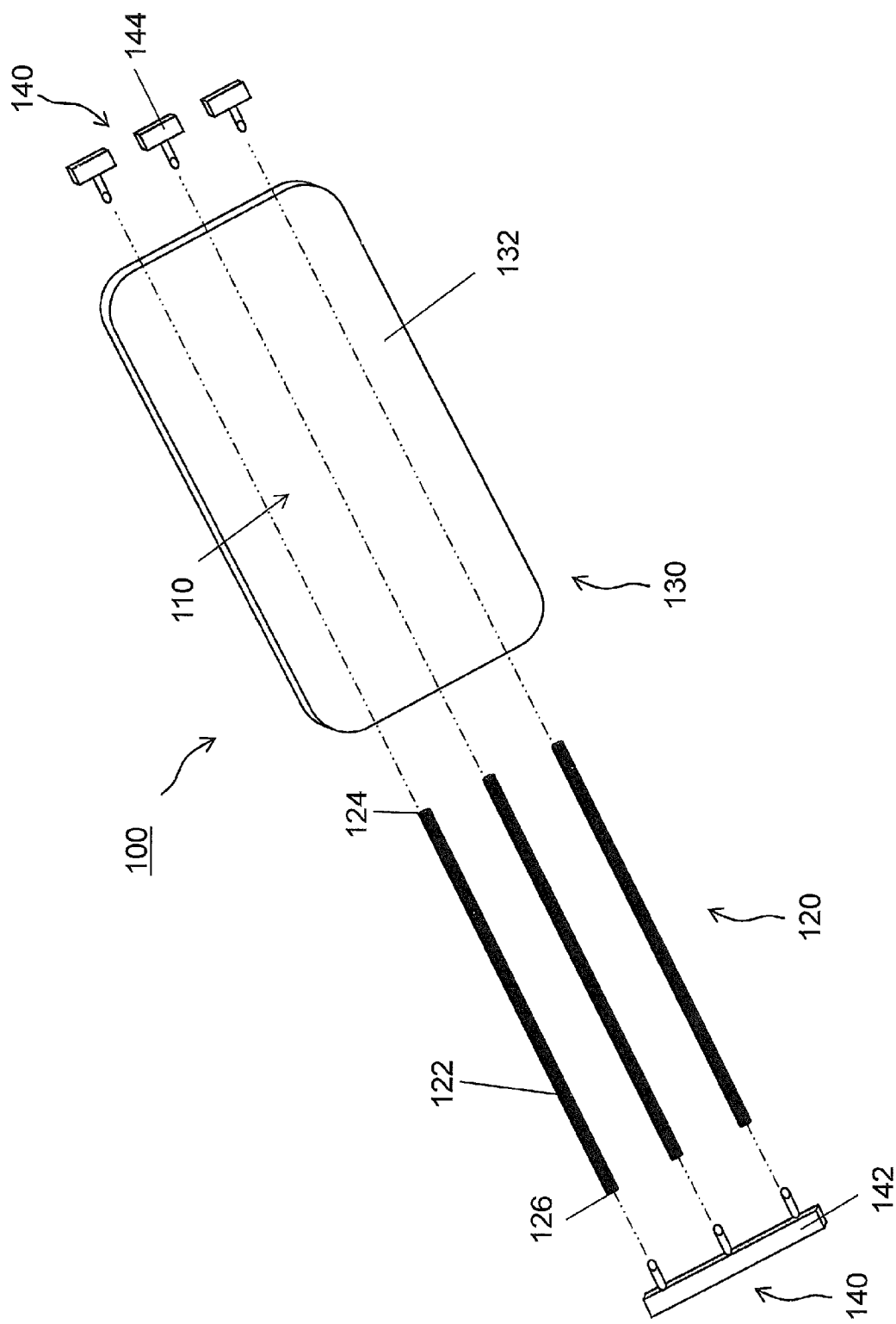
FIG. 3 illustrates an exploded view of the breastfeeding assistance device according to one embodiment of the invention.
Figure 4:
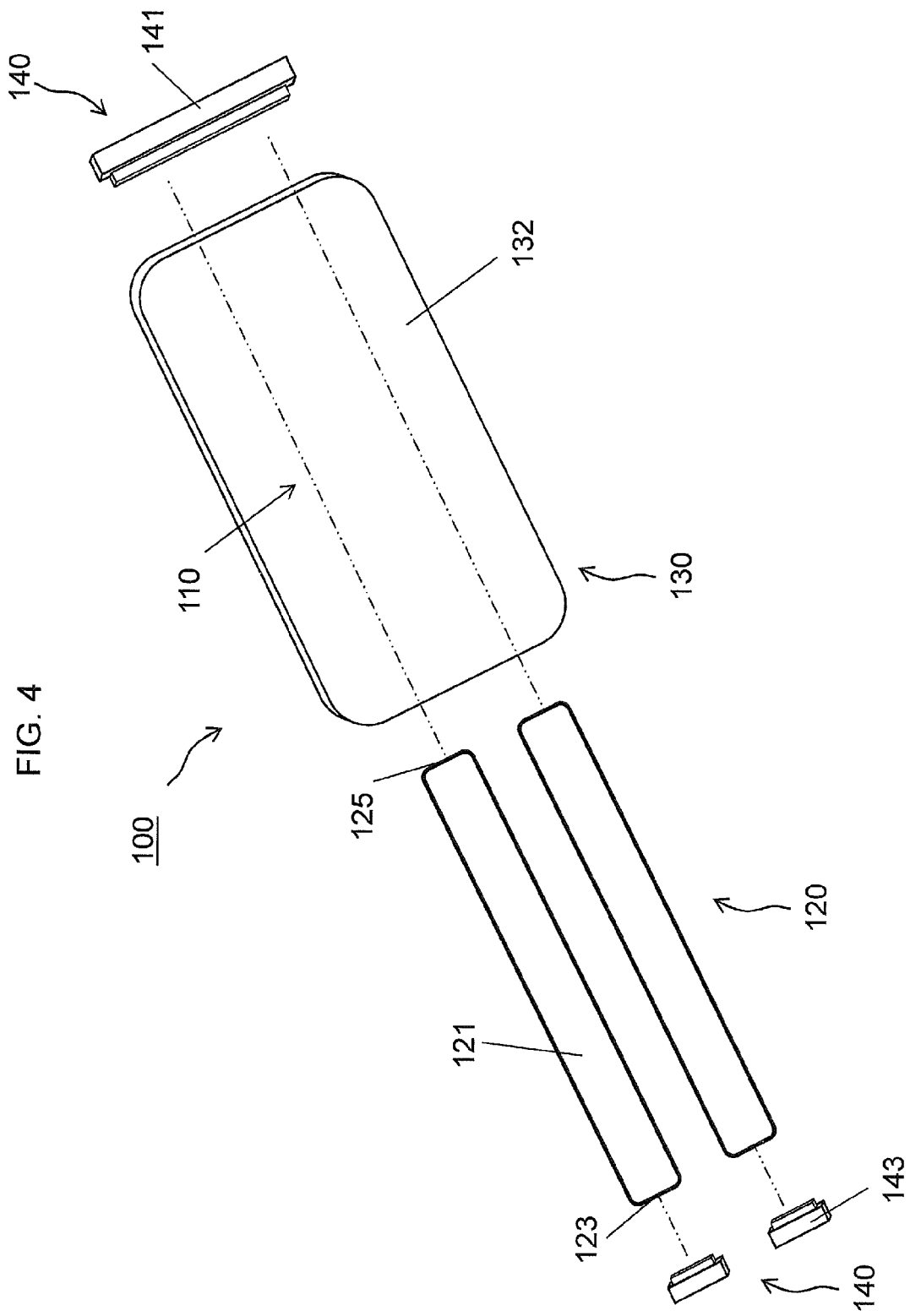
FIG. 4 illustrates an exploded view of the breastfeeding assistance device according to another embodiment of the invention.

As shown in FIG. 3 and FIG. 4, the body 110 includes a core portion 120 and an exterior portion 130. The core portion 120 is composed of a material that is bendable and/or twistable into a selected configuration and self-sustainable in that configuration until the device 100 is manually shaped into another configuration. In other words, the core portion 120 is flexible, but relatively non-resilient. Examples of materials include those referred to as "medium stuff" or "half hard" and may include, for example, aluminum, copper, iron, lead, nickel, silver, titanium, tin, zinc and all related alloys such as steel.

The exterior portion 130 is joined to and covers a majority of the core portion 120. The exterior portion 130 is substantially immovable relative to the core portion 120. The exterior portion 130 includes an outer surface 132 having a coefficient of friction that engages skin and resists slipping. The exterior portion 130 is composed of a flexible, substantially impermeable material that is also comfortable against the skin such as any polymer. Polymers may include, for example, elastomers and polyurethanes.

As shown in FIG. 3 and FIG. 4, to securely join the core portion 120 and the exterior portion 130, one or more fastening elements 140 may be provided. Similar to the exterior portion 130, the fastening elements 140 may be composed of a bendable and/or twistable material.

FIG. 3 illustrates an embodiment of the invention in which the core portion 120 comprises one or more rod elements 122. Each rod element 122 includes a first end 124 and a second end 126 and may be a wire. The fastening element 140 connects to an end 124, 126 of the rod element 122. In one embodiment, the fastening element 140 is a unitary component 142 that connects to one end 124, 126 of two or more rod elements 122. In another embodiment, the fastening element 140 comprises one or more individual components 144 that each connects to one end 124, 126 of the rod element 122.

FIG. 4 illustrates an embodiment of the invention in which the core portion 120 comprises one or more plate elements 121. Each plate element 121 includes a first end 123 and a second end 125 and may be a thin sheet or strip. The fastening element 140 connects to an end 123, 125 of the plate element 121. In one embodiment, the fastening element 140 is a unitary component 141 that connects to one end 123, 125 of two or more plate elements 121. In another embodiment, the fastening element 140 comprises one or more individual components 143 that each connects to one end 123, 125 of the plate element 121.

It is contemplated the device 100 may include fastening elements 140 comprised of one or more unitary components, one or more individual components, or a combination of both as illustrated in FIG. 3 and FIG. 4. However, it is also contemplated that certain embodiments of the invention may not require any fastening components, for example, devices that are manufactured using a dip molding process.

Figure 5B:
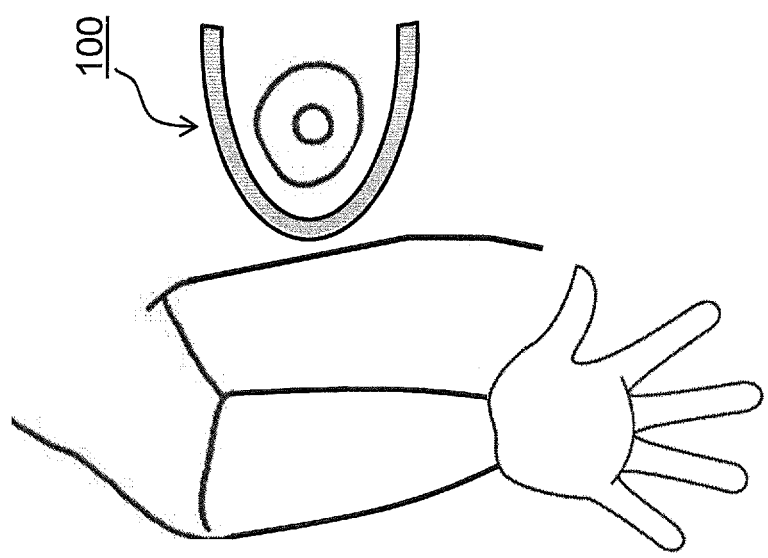
FIG. 5B illustrates the breastfeeding assistance device according to the invention in the configuration of a "U" hold.
Figure 5A:
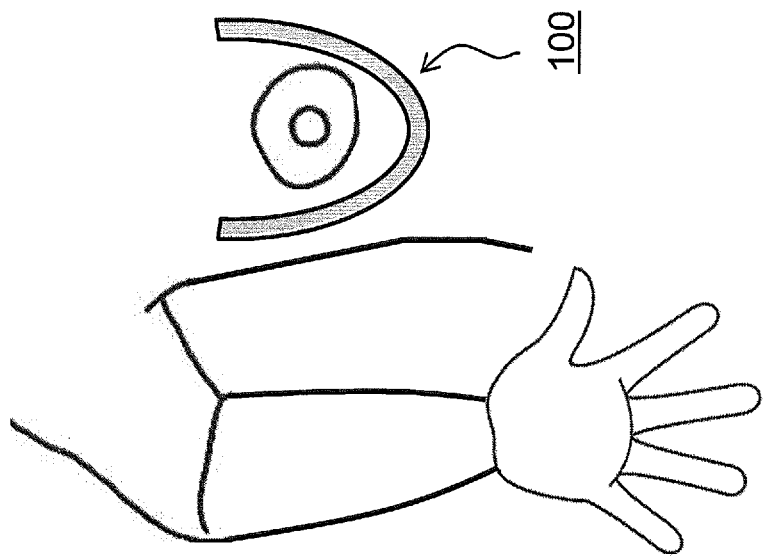
FIG. 5A illustrates the breastfeeding assistance device according to the invention in the configuration of a "C" hold.

When breastfeeding, the approximate center of the device 100 is placed on the breast and each end of the device 100 is manually shaped around the breast into a configuration that squeezes or compresses the breast. The breastfeeding assistance device is self-sustaining in that configuration. The breastfeeding assistance device assists with the support and manipulation of a mother's breast during breastfeeding as well as allows at least one hand free. FIG. 5A illustrates the device 100 in a "C" hold configuration and FIG. 5B illustrates the device 100 in a "U" hold configuration.

While the disclosure is susceptible to various modifications and alternative forms, specific exemplary embodiments of the present invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

The invention claimed is:

1. A bendable breastfeeding assistance device, comprising:
    a generally thin rectangular body including a core portion and an exterior portion, the core portion comprising a bendable rod element or a bendable plate element, and a flexible substantially non-absorbent exterior portion connected to and covering a majority of the core portion and being substantially immovable relative to the core portion, the exterior portion having an outer surface that includes a coefficient of friction that engages skin and resists slipping, a fastening element securely joining the core portion and the exterior portion with the fastening element connecting to an end of the bendable rod element or the bendable plate element, the device including a form that compresses a breast and is self-sustaining in the form until the device is manually shaped into another form.

2. The bendable breastfeeding assistance device according to claim 1 wherein the exterior portion comprises a polymer material.

3. The bendable breastfeeding assistance device according to claim 1 wherein the exterior portion comprises an elastomer material.

4. The bendable breastfeeding assistance device according to claim 1 wherein the exterior portion comprises a polyurethane material.

5. The bendable breastfeeding assistance device according to claim 1 wherein the core portion comprises one or more materials selected from the group of aluminum, copper, iron, lead, nickel, silver, titanium, tin, zinc, steel.

6. A breastfeeding assistance device, comprising:
    a generally thin body including a core portion and an exterior portion, the core portion comprising one or more bendable rod elements, and a flexible substantially non-absorbent exterior portion connected to and covering a majority of the one or more bendable rod elements and being substantially immovable relative to the one or more bendable rod elements, the exterior portion having an outer surface that includes a coefficient of friction that engages skin and resists slipping, a fastening element securely joining the core portion and the exterior portion with the fastening element connecting to an end of the one or more bendable rod elements, the device including a form that compresses a breast and is self-sustaining in the form until the device is manually shaped into another form.

7. The breastfeeding assistance device according to claim 6 wherein the generally thin body is a rectangular body.

8. The breastfeeding assistance device according to claim 6 wherein the generally thin body is an oval body.

9. The breastfeeding assistance device according to claim 6 wherein the exterior portion comprises a polymer material.

10. The breastfeeding assistance device according to claim 6 wherein the exterior portion comprises an elastomer material.

11. The breastfeeding assistance device according to claim 6 wherein the exterior portion comprises a polyurethane material.

12. The breastfeeding assistance device according to claim 6 wherein the core portion comprises one or more materials selected from the group of aluminum, copper, iron, lead, nickel, silver, titanium, tin, zinc, steel.

13. A breastfeeding assistance device, comprising:
a generally thin body including a core portion and an exterior portion, the core portion comprising one or more bendable plate elements, and a flexible substantially non-absorbent exterior portion connected to and covering a majority of the one or more bendable plate elements and being substantially immovable relative to the one or more bendable plate elements, the exterior portion having an outer surface that includes a coefficient of friction that engages skin and resists slipping, a fastening element securely joining the core portion and the exterior portion with the fastening element connecting to an end of the one or more bendable plate elements, the device including a form that compresses a breast and is self-sustaining in the form until the device is manually shaped into another form.

14. The breastfeeding assistance device according to claim 13 wherein the generally thin body is a rectangular body.

15. The breastfeeding assistance device according to claim 13 wherein the generally thin body is an oval body.

16. The breastfeeding assistance device according to claim 13 wherein the exterior portion comprises a polymer material.

17. The breastfeeding assistance device according to claim 13 wherein the exterior portion comprises an elastomer material.

18. The breastfeeding assistance device according to claim 13 wherein the exterior portion comprises a polyurethane material.

19. The breastfeeding assistance device according to claim 13 wherein the core portion comprises one or more materials selected from the group of aluminum, copper, iron, lead, nickel, silver, titanium, tin, zinc, steel.

\* \* \* \* \*